(12) United States Patent
Pipers

(10) Patent No.: US 6,939,881 B2
(45) Date of Patent: Sep. 6, 2005

(54) METHODS FOR PREVENTION OF ULCERS AND IMPROVING PHYSIOLOGICAL PERFORMANCE

(76) Inventor: Frank Pipers, 955 Juniper St., NE., Atlanta, GA (US) 30309

(*) Notice: Subject to any disclaimer, the term of this patent is extended or adjusted under 35 U.S.C. 154(b) by 0 days.

(21) Appl. No.: 09/867,285

(22) Filed: May 29, 2001

(65) Prior Publication Data

US 2002/0065306 A1 May 30, 2002

Related U.S. Application Data

(60) Provisional application No. 60/207,878, filed on May 30, 2000.

(51) Int. Cl.[7] ...................... A61K 31/44; A61K 31/495; A61K 31/50
(52) U.S. Cl. .............. 514/335; 514/252.12; 514/253.03
(58) Field of Search ............................ 514/335, 252.12, 514/255.03

(56) References Cited

FOREIGN PATENT DOCUMENTS

| WO | 9631213 | 10/1996 |
|---|---|---|
| WO | 0050038 | 8/2000 |

OTHER PUBLICATIONS

Canine Nutrition, www.knowbetterdogfood.com/dogcare/health/nutrition.php, 2001.*
Tufts University School of Veterinary Medicint, Horse Gastric Ulcer Bulletin, www.tufts.edu/vet/sports/ulcers.html, 2002.*
Papids, Gastroenterology, the 90's vol. 23, No. 3, 1993, 497–512.
FDA Federal Register, 64(72), Apr. 15, 1999, 18572–18573.
Meinichouk et al, Canadian J. Vet Res 103(4), 248–252, 1999.
Smith, Vet. Human Toxicol, 40(Suppl 1) 1998, 29–34.

* cited by examiner

*Primary Examiner*—Rebecca Cook
(74) *Attorney, Agent, or Firm*—Frommer, Lawrence & Haug; Thomas J. Kowalski; Judy Jarecki-Black

(57) ABSTRACT

Methods for preventing ulcers, such as gastric ulcers, in a horse about to undergo stress that causes gastric ulcers and prior to occurrence of a gastric ulcer condition in the horse involving administering a proton pump inhibitor (PPI) are disclosed and claimed.

11 Claims, No Drawings

METHODS FOR PREVENTION OF ULCERS AND IMPROVING PHYSIOLOGICAL PERFORMANCE

This application claims priority of Ser. No. 60/207,878 filed May 30, 2000.

FIELD OF THE INVENTION

The present invention provides a method for the prevention of ulcers in animals, including horses, dogs and humans.

BACKGROUND

The development of endoscopes able to visualize the stomach of horses showed that the frequency of gastric ulcers in horses is higher than presumed. The aetiology of gastric ulcers in horses is not well known but it is assumed that stress plays an important role in some cases.

It is well-known to treat gastric ulcer in horses and foals by the administration of a proton pump inhibitor which is preferably 5-metoxy-2-[[(4-metoxy-3,5-dimethyl-2-pyridinyl)methyl]sulphinyl]-1H-benzimidazole, whose common name is Omeprazole. A paste for horses containing 37% w/w. Omeprazole is marketed under the trade name Gatrogard for the treatment of ulcers. Generally, this paste is to be administered orally once a day for 4 weeks at the dosage of 1.8 mg omeprazole/lb body weight (4 mg/kg). Thereafter, recurrence of gastric ulcers can be prevented if the treatment is continued for at least an additional 4 weeks at a lower dose of 0.9 mg/lb (2 mg/kg).

Proton pump inhibitors (PPI) are potent inhibitors of gastric acid secretion by inhibiting $H^+K^+$-ATPase, the enzyme involved in the final step of hydrogen ion production in the parietal cells.

The PPI omeprazole is disclosed in U.S. Pat. No. 4,255,432.

Pharmaceutical compositions containing proton, pump inhibitors are also disclosed in the PCT Patent Application WO 96/31213 and U.S. Pat. No. 5,708,017 which discloses a stable, ready-to-use oral paste composition of proton pump inhibitor, such as, for example, omeprazole.

Another oral composition containing proton pump inhibitor is known from WO 94/25070 in the form of enteric coated dry particles mixed with a dry gelling agent.

For a good review of the diagnostic and treatment of equine gastric ulcer syndrome (EGUS) or gastrointestinal ulcers, see EQUINE VETERINARY EDUCATION (1999) 11 (5) 262–272.

While treatment of ulcers and prevention of recurrence of the treated ulcers is known and is efficient, no method of prevention of ulcers, including gastric ulcers in animals, including horses and dogs where ulcers are relatively frequent, is known and it was believed that such prevention would be very difficult. Moreover, the far insufficient knowledge of the aetiology of the ulcers added to the difficulty of conceiving a method able to prevent occurrence of ulcers in animals.

OBJECTS AND SUMMARY OF THE INVENTION

The present invention provides a method for the prevention of gastric ulcers, such as gastrointestinal ulcers in a mammal, e.g. a domestic mammal, a farm mammal, a companion mammal, a game or sport mammal, such as horses, dogs, humans, and other mammals that may be susceptible to such ulcers. The method comprises administering e.g., periodically, an effective amount of a proton pump inhibitor to the mammal. The administration can be prior to or during a stressful event. It can also be a single treatment or administration over one or two days. This administering can be of amounts used in animals for the treatment of ulcers, although lower or higher doses can also be employed.

This prevention of gastric ulcers is in mammals prior to the occurrence of a gastric ulcer condition and is in contrast to treatment or prevention of reoccurrence in an animal that has already had a gastric ulcer condition.

The invention also provides the use of a proton pump inhibitor, preferably omeprazole, for the prevention of gastric ulcers in mammals.

DETAILED DESCRIPTION

The proton pump inhibitors used in the present invention can include compounds of the general formula:

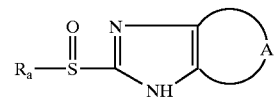

wherein $R_a$ is

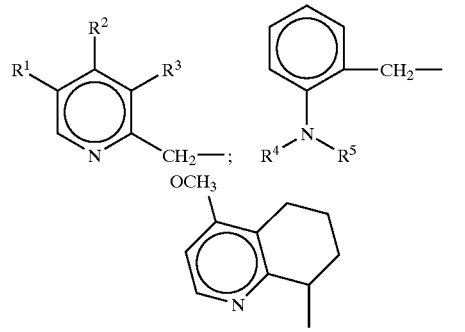

Where $R^1$ and $R^3$ are independently selected from hydrogen, lower alkyl, lower alkoxy and halogen, $R^2$ is selected from hydrogen, lower alkyl, lower alkoxy-lower alkoxy, lower fluoralkoxy and

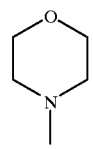

$R^4$ and $R^5$ are independently selected from lower alkyl, A is

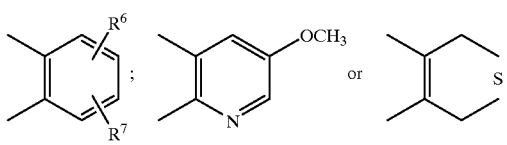

$R^6$ and $R^7$ are independently selected from hydrogen, lower alkyl, lower alkoxy, lower fluoralkoxy, lower fluoroalkyl, halogen,

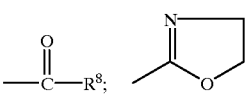

wherein R[8] is lower alkyl or lower alkoxy.

Examples of proton pump inhibitors according to Formula I

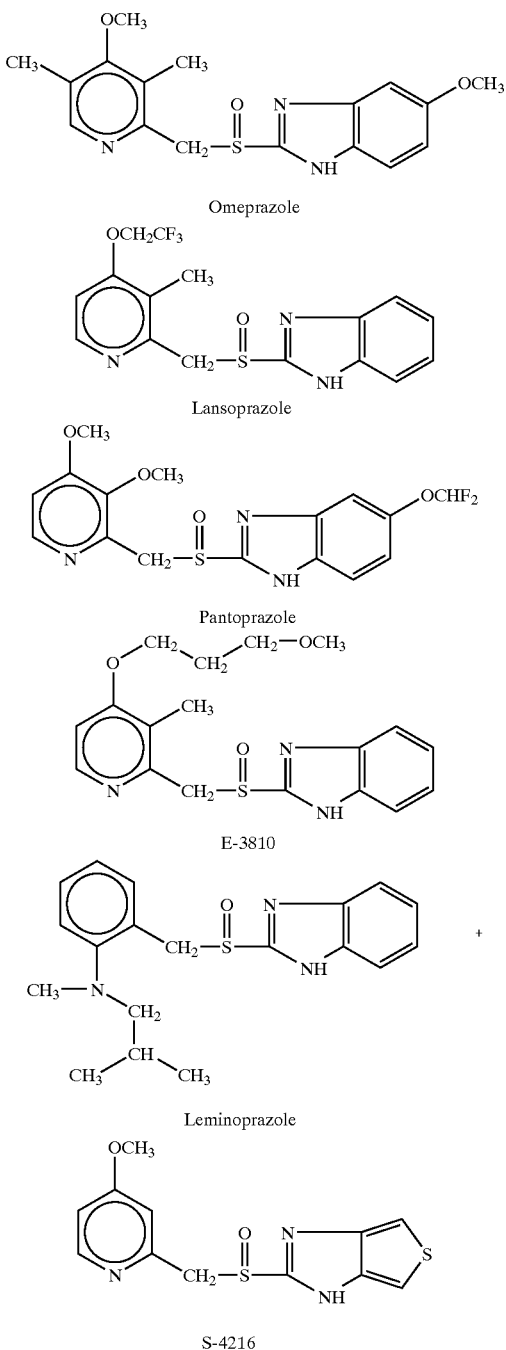

Examples of other PPI include esomeprazole (nee: perprazole), rabeprazole, and IY-81149 (distributed by Axican Pharma).

The preferred proton pump inhibitor used in the present invention is the compound known as omeprazole.

The proton pump inhibitors used in the present invention are known compounds in the art. and methods for their preparation may be found in the literature. For example, omeprazole is disclosed in EP 5129, lansoprazole in EP 174.716, pantoprazole in EP 166,287, leminoprazole in GB 2,163,747, rabeprazole in U.S. Pat. No. 5,045,552.

The preferred compound for horses and dogs is omeprazole.

Omeprazole is also preferred for humans.

The periodic treatment is preferably a daily treatment. However, a single treatment or administration of a PPI or over one or two days (e.g., once daily for one or two days), such as prior to or during a stressful event, is also envisioned.

The effective amount of proton pump inhibitor is preferably of 0.1 to 8 mg per kilogram body weight.

It is preferred to administer relatively low doses, preferably equal or more preferably, less than the usual doses for the treatment of ulcers in the animal.

More preferably, the dose is about 50% of the usual dose for the treatment in the animal.

In order to maintain relatively low blood levels of the proton pump inhibitor, the compound is administered daily but this frequency can be lowered, e.g. to every other day or once every three days or once weekly, for compounds which persist for a long time in the organism.

As an alternative, the treatment can include administration of the compound in the form of a formulation for controlled release and long lasting delivery, in which case the administration can be less frequent, for example, a weekly or a monthly administration.

The duration of the treatment for preventing ulcers is preferably at least several days.

More preferably the treatment for prevention is a continuous treatment, either for life or at least during the whole period where the animal is or is suspected to be under stress conditions or other conditions which may increase the risk of formation of ulcers.

Preferably the treatment is conducted on animals having substantial risk of developing gastrointestinal ulcers. For example, for horses the treatment is more preferably administered during periods of stress, training, transportation, change in environment (weather changes, housing changes) or pregnancy.

According to the invention, the inhibitor can be administered under any suitable formulation for delivery, preferably for oral delivery.

Suitable oral formulations include oral solutions, oral suspensions, feed premix, pastes, gels, granules, tablets, capsules or boli.

Preferably the proton pump inhibitor is provided for horses as a pharmaceutical composition for oral administration comprising a proton pump inhibitor, a thickening agent, a basifying agent, and a hydrophobic, oily liquid vehicle. Preferably these formulations make a paste for horses. Such formulations are disclosed in PCT Patent WO 96/31213 and U.S. Pat. No. 5,708,017 which are hereby incorporated by reference.

Other oral formulations can be made in the form of enteric dry particles mixed with a dry gelling agent.

The following formulations are preferred for humans: oral solutions or suspensions, gels, tablets, capsules or powder.

The efficiency of the method for preventing significant or persistent ulceration was completely unexpected. The invention also provides the use of a proton pump inhibitor, preferably omeprazole, for the preparation of a formulation for the prevention of gastric ulcers in mammals.

It also provides formulations prepared according to said use and comprising an amount of PPI which is less, preferably 50%, than the usual dose for preventing ulcers for the same mammal.

The invention will be further described in the following non limiting examples.

EXAMPLES

The following exemplifies a comparative method showing the efficiency of a formulation according to the invention for the prevention of gastric ulcers in horses.

Example 1

Preparation of an Omeprazole-containing Oral Paste for Horses

The paste for horses, containing 37% w/w omeprazole can be prepared according to U.S. Pat. No. 5,708,017. This paste is contained in adjustable-dose syringes for oral delivery. In this example, the paste is the paste for horses sold in the United States under the trademark GASTROGARD.

Example 2

Feeding, Environmental and Training Regime for Race Horses

Objective

To determine the effects of gastric ulceration on the physiological responses in horses in simulated race training.

Horses were acclimatised for 2 weeks to the treadmill, following which they entered a standardised ascending training program for a 10 weeks. Ulcers were be induced in half of the horses during the second week by alternately withholding feed on alternate days. In brief, food, but not water, was withheld for periods of approximately 24 hours on days 14, 16, 18, 20 and 22. In horses in which ulceration was induced, bedding was removed from the stalls during periods when feed was withheld.

Feeding protocol

Alfalfa hay and grass hay were offered ad libitum. Ten kilograms oats was feed at 4 pm daily once the horses had entered their ascending exercise program.

Training Protocol

Horses were run on the treadmill 5 times/week.

For the first week, horses were walked (2 m/s) for 4 minutes, then trotted (4 m/s) for 3.5 minutes, after which they were galloped at approximately 9 m/s for a further 3 minutes. Horses were then removed from the treadmill, and allowed to cool off for approximately 30 minutes.

Following the initial physiological response evaluation (described below), the horses entered a standardised exercise protocol. The horses were initially walked (2 m/s) for 4 minutes, then trotted (4 m/s) for 3.5 minutes, after which they were galloped for a further 3 minutes at a speed such that they achieved a heart rate of 80% of their maximum heart rate (generally 10 to 11 m/s). The heart rate was monitored using telemetry equipment attached to their girths. Initially horses were run using this protocol 3 times per week, and were run at a speed producing 50% of their heart rate max on the remaining 2 days. However, there was a reduction in the severity of the ulceration using this regime, and consequently horses were run at a speed producing 80% of their heart rate max for 5 days per week.

Endoscopic Protocol

Horses were examined endoscopically approximately every week. Ulcers were scored for their location and severity using the following system:

Location of Gastric Ulcer

MPGC Squamous mucosa adjacent to margo plicatus, greater curvature

MPRT Squamous mucosa adjacent to margo plicatus, right side

LC Squamous mucosa adjacent to margo plicatus, lesser curvature

SF Squamous mucosa, dorsal fundus

GF Glandular mucosa, fundus

Ulcer Scoring System

0. Normal mucosa—no ulcer or ulcers completely resolved.
1. Mild ulceration—multifocal or generalized areas appearing to be superficial ulcerations with or without hyperemia and mild/moderate hyperkeratosis.
2. Moderate ulceration—extensive superficial appearing lesions of deeper focal lesions with or without some mucosal proliferation along lesion margins and small amount of bleeding.
3. Severe ulceration—deep appearing multifocal or generalized ulceration with or without moderate mucosal proliferation along lesion margins and active hemorrhage.

Testing Physiological Responses

An evaluation was conducted on all horses prior to the induction of gastric ulceration, and at the completion of the study. Prior to the evaluation, horses were instrumented with an ECG and a venous catheter. A gas collection mask was placed over the horse's nose and mouth to measure the oxygen and carbon dioxide content of the expired air. $Vo_2$ and $Vco_2$ were determined from standard equations. The horses performed a standardised test consisting of walking at 2 m/s for 4 minutes, then trotting at 4 m/s for 3.5 minutes, and then galloping at approximately 15 m/s until "exhaustion" (defined as when the horse could no longer maintain the speed of the treadmill). Heart rate was determined by counting the number of QRS complexes on a 15-second trace. Blood lactate values was measured in blood taken from the 14-gauge jugular cartheter and placed in fluoride-oxalate tubes. The $Vo_2$ and $Vco_2$ and HR measurements are taken when they had reached a steady state.

Results

Ulcer Severity

Ulcers were induced in all horses subjected to the alternate withholding of feed. Ulcers were maintained in the horses within the ulcer group, although during the period when horses were running at a lower intensity (ie at 50% heart rate max two times per week). However, when the intensity of the treadmill exercise was increased, the ulcers returned to their original severity. Ulcers were maintained in the ulcer group for the duration of the study. There was a significant difference in the severity of gastric ulceration between the ulcer group and the control group (p=0.001).

Others

The lactate concentrations measured were consistent with the horses reaching their anaerobic threshold. Heart rate was not significantly altered in either group when the initial evaluation was compared to the final evaluation. There were no differences in the weight of the horses between groups.

The time to exhaustion was increased whether ulcers had been induced or not. However, the amount of the increase was greater in those horses in which ulcers had not been induced compared to the horses in which ulcers had been induced (P=0.3). There was a marked trend for the stride length of the control horses to increase by a greater amount.

When compared to the first evaluation, horses within the control group were run at a faster speed than horses in the ulcer group (P=0.13). At the final evaluation, the $VO_2$ increased by 38% for the control horses compared to 8% for the ulcer group (P=0.02). This would represent an approximately 4.5 improved response to training for the control horses compared to the ulcer horses.

It results that this protocol is a treatable protocol to induce stress-generated gastric ulcers.

Example 3

Prevention of Gastric Ulcers in Horses

Horses submitted to the training protocol according to example 2 were divided into two groups of 14 horses each group. They were then handled and identically trained for 56 days in the trial according to example 2 to induce gastric ulcers.

Group 1 received the horse paste formulation of example 1 at 4 mg/kg omeprazole while Group 2 received no medication.

Within two weeks all of the non-treated horses developed moderate to severe ulcers that remained or worsened during the trial.

In the treated group only two horses developed mild ulcers that did not persist for more than ten days during the trial.

At the end of the trial, horses in the omeprazole-treated group demonstrated physiological responses that were significantly better compared to the non-treated group. Oxygen consumption was substantially increased, as well as time to exhaustion and stride length.

What is claimed is:

1. A method for preventing occurrence of gastric ulcers in a horse about to undergo stress that causes gastric ulcers and prior to occurrence of a gastric ulcer condition in the horse, comprising administering to the horse an effective amount of omeprazole prior to, and optionally during, the stress.

2. The method of claim 1 wherein the administering is prior to and during the stress.

3. The method of claim 1, wherein the administering is daily.

4. The method of claim 1, wherein the gastric ulcers comprise gastrointestinal ulcers.

5. The method of claim 1 wherein the stress is training, transportation, change in environment, or pregnancy.

6. The method of claim 1, wherein the effective amount of omeprazole is 0.1 to 8 mg per kilogram body weight.

7. The method of claim 1, wherein the effective dose is about 50% of the usual dose for the treatment of ulcers in a horse.

8. The method of claim 1, wherein the effective dose is about 25% of the usual dose for the treatment of ulcers in a horse.

9. The method of claim 1, wherein the omeprazole is in the form of a formulation for controlled release.

10. The method of claim 1, wherein the administering is oral and the omeprazole is in a formulation for oral administration.

11. The method of claim 10, wherein the formulation is selected from the group consisting of oral solutions, oral suspensions, feed premix, pastes, gels, powder, granules, tablets, capsules and boli.

* * * * *